United States Patent [19]
Yoshida et al.

[11] Patent Number: 6,022,108
[45] Date of Patent: Feb. 8, 2000

[54] OPTHALMIC APPARATUS FOR JUDGING ALIGNMENT CONDITIONS BASED ON TARGET IMAGES

[75] Inventors: Makoto Yoshida, Gamagori; Munehiro Nakao, Toyokawa; Nobuo Suzuki, Nukata-gun, all of Japan

[73] Assignee: Nidek Co., Ltd., Aichi, Japan

[21] Appl. No.: 08/883,102

[22] Filed: Jun. 26, 1997

[30] Foreign Application Priority Data

| Jun. 28, 1996 | [JP] | Japan | 8-188564 |
| Jun. 28, 1996 | [JP] | Japan | 8-188565 |
| May 12, 1997 | [JP] | Japan | 9-137527 |

[51] Int. Cl.$^7$ ............................................. A61B 3/14
[52] U.S. Cl. ........................... 351/208; 351/211; 351/221
[58] Field of Search ........................... 351/205, 211, 351/208, 212, 221

[56] References Cited

U.S. PATENT DOCUMENTS

| 4,972,836 | 11/1990 | Schenck et al. | 128/653 |
| 4,995,393 | 2/1991 | Katsuragi et al. | 128/648 |
| 5,279,300 | 1/1994 | Miwa et al. | 128/648 |
| 5,302,979 | 4/1994 | Maeda et al. | 351/212 |
| 5,406,076 | 4/1995 | Mimura et al. | 250/229 |
| 5,463,430 | 10/1995 | Isogai et al. | 351/208 |
| 5,502,521 | 3/1996 | Katou | 351/221 |
| 5,532,769 | 7/1996 | Miwa et al. | 351/205 |
| 5,557,350 | 9/1996 | Yano | 351/208 |
| 5,596,377 | 1/1997 | Yano | 351/211 |
| 5,696,573 | 12/1997 | Miwa | 351/208 |
| 5,844,659 | 12/1998 | Isogai | 351/208 |

FOREIGN PATENT DOCUMENTS

| 57-81324 | 5/1982 | Japan . |
| 4-297226 | 10/1992 | Japan . |
| B2-5-56133 | 8/1993 | Japan . |
| 6-7292 | 1/1994 | Japan . |
| 7-88080 | 4/1995 | Japan . |
| 7-299037 | 11/1995 | Japan . |
| 8-562 | 1/1996 | Japan . |
| 8-565 | 1/1996 | Japan . |
| 2 293 659 | 4/1996 | United Kingdom . |
| 2 294 543 | 5/1996 | United Kingdom . |
| 92/21999 | 12/1992 | WIPO . |

*Primary Examiner*—Huy Mai
*Attorney, Agent, or Firm*—Oliff & Berridge, PLC

[57] ABSTRACT

An ophthalmic apparatus having measurement device for inspection or measurement, and bringing the measurement device into the predetermined positional relationships relative to an eye to be examined, the ophthalmic apparatus providing a moving device for moving the measurement device relatively to the eye to be examined, an alignment target projecting optical system for projecting plural alignment targets onto the periphery of cornea of the eye to be examined, an alignment target detecting optical system for detecting target images which are formed by projecting the alignment targets, a judging device for judging the alignment condition in vertical and lateral direction based on the number and positional relationships of target images which are detected, and an instruction device for instructing the moving device to move based on the result judged by the judging device.

16 Claims, 12 Drawing Sheets

DISTRIBUTION OF THE LIGHT VOLUME ON LINE A-A

DISTRIBUTION OF THE LIGHT VOLUME ON LINE B-B

OPTHALMIC APPARATUS FOR JUDGING ALIGNMENT CONDITIONS BASED ON TARGET IMAGES

BACKGROUND OF THE INVENTION

1. Field of the Invention

The present invention relates to an ophthalmic apparatus and more particularly, relates to the ophthalmic apparatus for bringing the apparatus into the predetermined positional relationships relative to an eye to be examined.

2. Description of Related Art

An eye refractive power measurement apparatus for measuring refractive power of the eye to be examined, a non-contact tonometer for measuring an intraocular pressure and so on need an alignment adjustment in order to bring the measurement optical system into the predetermined positional relationships relative to an eye to be examined.

As alignment mechanism for such kinds of apparatus, such alignment mechanism is known that an alignment target is projected from an optical axis of an eye to be examined, then a reflecting luminance close to a cornea vertex which is formed by a cornea reflection is photographed by TV camera in order to display it onto TV monitor for use in observation. An examiner performs an alignment adjustment of vertical and horizontal directions so that the reflecting luminance of the cornea may come to be the predetermined positional relationships relative to a reticle. Also, the examiner performs the alignment adjustment of working distance (forward and backward) directions by bringing the reflecting luminance of the cornea into focus.

SUMMARY OF THE INVENTION

However, referring to such alignment method as described above, the cornea vertex is defined as a standard, therefore if the cornea vertex is out from the photographing screen, then the luminance cannot be observed and detected, so it is mentioned that the detecting range of alignment is not necessarily wide. In the case that the luminance cannot be observed on the TV monitor for use in observation, the apparatus is moved on the basis of an anterior image of the eye to be examined and so on in order to make the luminance be observed, however an unskilled-examiner having difficulty in inspection does not recognize clearly which direction the apparatus should be moved, therefore it results in such disadvantages that it takes much time to perform an alignment.

Further, in the case of an alignment device which controls a driving means based on a detected information of a luminance of a cornea vertex, there is such disadvantage that if the luminance of the cornea vertex cannot be detected, then the driving means cannot be driven.

The present invention has been made in view of the above circumstances and has an object to overcome the above problems and to provide an ophthalmic apparatus which may perform an alignment easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus having measurement means for inspection or measurement, and bringing the measurement means into the predetermined positional relationships relative to an eye to be examined of this invention comprises moving means for moving the measurement means relatively to the eye to be examined, alignment target projecting optical system for projecting plural alignment targets onto the periphery of cornea of the eye to be examined, alignment target detecting optical system for detecting target images which are formed by projecting the alignment target, judging means for judging the alignment condition in vertical and lateral direction based on the number and positional relationships of target images which are detected, instruction means for instructing the moving means to move based on the result judged by the judging means.

In another aspect of the present invention, the apparatus comprises moving means for moving measurement part relatively to the eye to be examined, first alignment target projecting optical system for projecting the first alignment target to the cornea center of the eye to be examined, second alignment target projecting optical system for projecting the plural targets to the periphery of cornea of the eye to be examined, alignment target detecting optical system for detecting target images which are formed by projecting targets by the first and second alignment target projecting optical systems, judging means for judging the alignment condition in vertical and lateral direction based on the number and relationships of target images detected by the alignment target detecting optical system, and instruction means for instructing the moving means to move based on the result judged by the judging means.

According to the present invention, it is capable of making the detecting range wide by projecting the plural targets onto the cornea, therefore the alignment comes to be easier.

Also, a highly-reliable measurement result can be obtained without performing an useless measurement due to an eye-fixation deviation.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
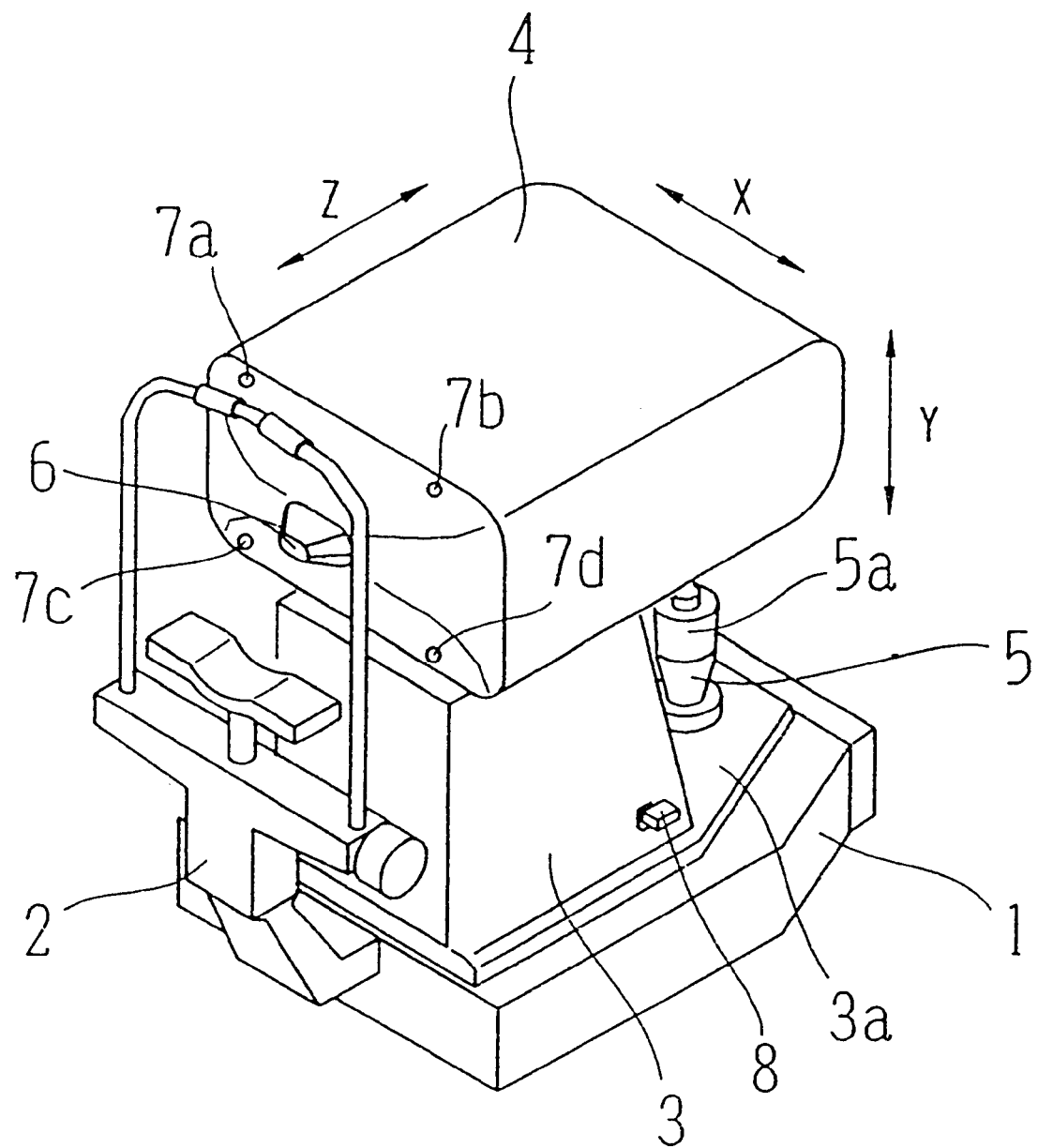
FIG. 1 is an overview showing a schematic configuration of a noncontact tonometer of a preferred embodiment.

FIG. 1 shows the schematic overview of the noncontact tonometer of an preferred embodiment. Reference numeral 1 denotes a base to which a jaw stand 2 is fixed for fixing an eye to be examined. 3 is a body part, 4 is a measurement part which stores the optical system mentioned-below, and 5 is a joystick which is used in order to move the body part 3 and the measurement part 4. The body part 3 moves smoothly along a horizontal plane of the base 1 in forward and backward direction (Z-direction) and in right and left direction (X-direction) by operating the joystick 5, and the measurement part 4 moves in vertical direction (Y-direction) relative to the body part 3 by operating the joystick 5.

Concerning the movement of the body part 3 relative to the base 1, a fine movement thereof in horizontal direction is realized due to the construction of a spherical part and a lower edge which are formed at a lower place of the shaft of the joystick 5, a sliding plate of which a lower edge swings, a friction plate which touches the sliding plate and is attached to the base 1, and a spherical bearing inside a housing 3a which is united with the body part 3 in a body. The rotating direction and the amount of rotation are detected based on a signal transmitted from a light-receiving element that are caused by a rotation knob 5a around the outer circumference of the joystick 5, a slit plate which rotates with the rotation knob 5a, and a light source and a light-receiving element disposed at the shaft putting the slit plate therebetween, then on the basis of the detected result, the upper and lower movement of the measurement part 4 relative to the body part 3 is performed by driving and controlling the Y-axis motor which moves the measurement part 4 in vertical direction. A detailed description for these mechanisms concerning the joystick is disclosed in Japanese Patent Publication No.HEI6(1994)-7292 corresponding to U.S. Pat. No. 5,406,076 (title of the invention: Joystick mechanism for ophthalmic apparatus) by the applicant of the present invention, so see this reference.

Also, the measurement part 4 moves relative to the body part 3 in right and left direction (X-direction) and in forward and backward direction (Z-direction). These movements are caused by a X-axis motor and a Z-axis motor which are driven and controlled by a control circuit mentioned-below.

6 is a nozzle part at which a nozzle for gushing compressed-gas out to the eye to be examined is disposed. On the examine side of the measurement part 4, the four light sources 7a to 7d (corresponding to a light source of the second alignment target projecting optical system mentioned-below) which project the alignment targets at periphery of the cornea of the eye to be examined as centering the nozzle part 6 are disposed. On the side part of the body part 3, a knob 8 is disposed in order to restrict the moving limits toward the eye to be examined for the nozzle part 6. Also, the TV monitor for use in observation is provided for the joystick 5 side (the examiner side) of the body part 3.

[Optical system]

Figure 2:
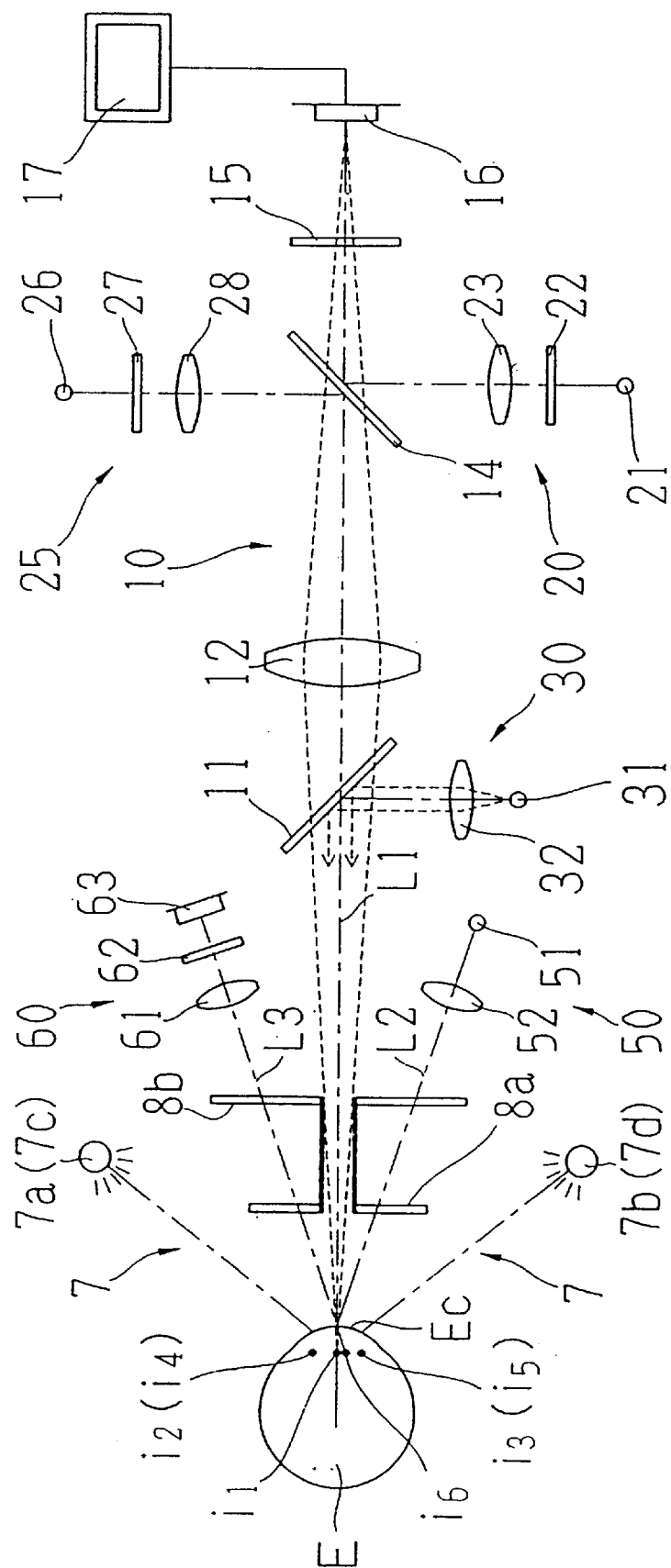
FIG. 2 is a view showing a configuration of an important part of an alignment optical system of a noncontact tonometer of a preferred embodiment.

FIG. 2 shows an important part of a configuration of the alignment optical system of the apparatus, and is from a top point of view. Besides, the noncontact tonometer measures interocular pressure based on the gas pressure which is detected directly or indirectly by gushing the compressed-gas out to the cornea of the eye to be examined to modify it to be the predetermined shape, however this measurement device has little relationships with the present invention, therefore the description is omitted. A detailed description is disclosed in Japanese Patent Publication No.HEI4(1992)-297226 corresponding to U.S. Pat. No. 5,279,300 (title of the invention: Noncontact type tonometer) by the applicant of the present invention, so see this reference.

(Observation Optical System)

10 is an observation optical system of which the optical axis is denoted by $L_1$. The observation optical system 10 also serves as a target detecting optical system which detects the targets (mentioned-below) for use in the first and second alignment in vertical and horizontal direction. On the optical path of the observation optical system 10, the nozzle 9 which gushes gas for use in modifying the cornea out is disposed with being held by glass plates 8a and 8b, and the axis thereof and the optical axis $L_1$ coincide. On the optical axis $L_1$, a beam splitter 11, an objective lens 12, a beam splitter 14, a filter 15, and a CCD camera 16 are disposed. The filter 15 has such characteristics that it transmits light bundles (wavelength 950 nm) of the first and second alignment target optical system (mentioned-below) and light bundle (wavelength 950 nm) of a reticle projecting optical system (mentioned-below), and that it is does not transmits light bundle of the visible light and light bundle (wavelength 800 nm) of a distance target projecting optical system (mentioned-below) while prohibiting the unnecessary noise light from transmitting into the CCD camera 16. The anterior image and the target image photographed by the CCD camera 16 are displayed onto a TV monitor 17, and the examiner observes the images.

(Reticle Projecting Optical System)

20 denotes a reticle projecting optical system. 21 is a reticle projecting light source which emits the infrared light having wavelength of 950 nm, 22 is a reticle plate on which a circle-shaped mark is formed, and 23 is a projecting lens. The reticle on the reticle plate 22 which is illuminated by the reticle projecting light source 21 is photographed by the CCD camera 16 through the projecting lens 23, the beam splitter 14 and the filter 15.

Besides, light bundle emitted from the reticle projecting light source 21 of which output is modulated at the predetermined frequency in order to make detection of target images easy, thereby light bundle from the reticle projecting light source 21 is distinguished from light bundles emitted from the light sources 7a to 7d and light bundle emitted from the light source 31. Also, it is sufficient that the reticle image is observed on the TV monitor, therefore it may be distinguished based on the difference of luminance of target image by darkening, or it may be generated by a pattern generator electrically.

(Eye Fixation Optical System)

An eye-fixation optical system 25 includes a light source 26 which emitts visible light, an eye-fixation plate 27 and a projecting lens 28. Light bundle emerged from the eye-fixation plate 27 by turning on the light source 26 transmits into the eye E to be examined through the nozzle 9, via the projecting lens 28, the beam splitter 14, the objective lens 12, and the beam splitter 11.

(The First Alignment Target Projecting Optical System)

30 denotes the first alignment target projecting optical system. 31 is a central target-projecting light source, and 32 is a projecting lens. The light source 31 emitts infrared light having wavelength of 950 nm. Infrared light bundle emitted from the light source 31 is made to be parallel light bundle by the projecting lens 32, and then is reflected by the beam splitter 11, and is irradiated to the cornea Ec of the eye to be examined through the nozzle 9 along the optical axis $L_1$. Light bundle which is mirrored and reflected by the cornea Ec forms the first alignment target $i_1$ which is a virtual image of the light source 31. Light bundle of the first alignment target $i_1$ forms the image of the first alignment target $i_1$ on the photographing element of the CCD camera 16.

(The Second Alignment Target Projecting Optical System)

The second alignment target projecting optical system 7 includes four light sources 7a to 7d (see FIG. 1). The light sources 7a and 7b are disposed to be the same height with putting the optical axis $L_1$ therebetween whereby the optical distance of the targets are made to be the same, and the light sources 7c and 7d are disposed as the same. The light sources 7a to 7d emit infrared light having wavelength of 950 nm same as the light source of the first alignment target projecting optical system. Lights transmitted from the light sources 7a and 7b are irradiated from oblique-upper direction to the periphery of cornea of the eye E to be examined to form the target $i_2$ and $i_3$ which are virtual images of the light sources 7a and 7b. The light sources 7a and 7b are also used for detecting the opening-condition of eyelid (mentioned-below). Lights transmitted from the light sources 7c and 7d are irradiated from oblique-lower direction to the periphery of cornea of the eye E to be examined to form the target $i_4$ and $i_5$ which are virtual images of the light sources 7c and 7d. The light sources 7a to 7d are also used as illumination light sources which illuminate the anterior part of the eye to be examined.

Light bundles of four targets $i_2$, $i_3$, $i_4$, and $i_5$ transmit into the CCD camera 16 through the observation optical system 10 to form the image on the photographing element of the CCD camera 16.

(The Distance Target Projecting Optical System)

50 is a distance target projecting optical system of which optical axis is denoted by $L_2$. The optical axis $L_2$ is arranged so as to incline to the optical axis $L_1$, and both optical axes are intersecting at the position at interval of the predetermined working distance from the nozzle 9. 51 is a light source for projecting distance target, which emits light having wavelength of 800 nm differed from the light sources 7a to 7d and the light source 31, and 52 is a projecting lens.

Light emitted from the light source 51 is made to be parallel light bundle by the projecting lens 52, and is irradiated onto the cornea Ec along the optical axis $L_2$. Light bundle mirrored-and-reflected by the cornea Ec forms a target $i_6$ which is a virtual image of the light source 51.

(The Distance Target Detecting Optical System)

60 is a distance target detecting optical system of which the optical axis is denoted by $L_3$. The optical axis $L_3$ and the optical axis $L_2$ are symmetry with respect to the optical axis $L_1$, and both optical axes intersect on the optical axis $L_1$. On the optical axis $L_3$, a photo receiving lens 61, a filter 62 and an one-dimensional detecting element 63 are disposed. The filter 62 has such characteristics that it transmits through light bundle having wavelength of 800 nm from the light source 51, but does not transmits through light having wavelength 950 nm from the light sources 7a to 7d and the light source 31, and prohibits noise light from transmitting into the one-dimensional detecting element 63.

[The Control System]

Figure 3:
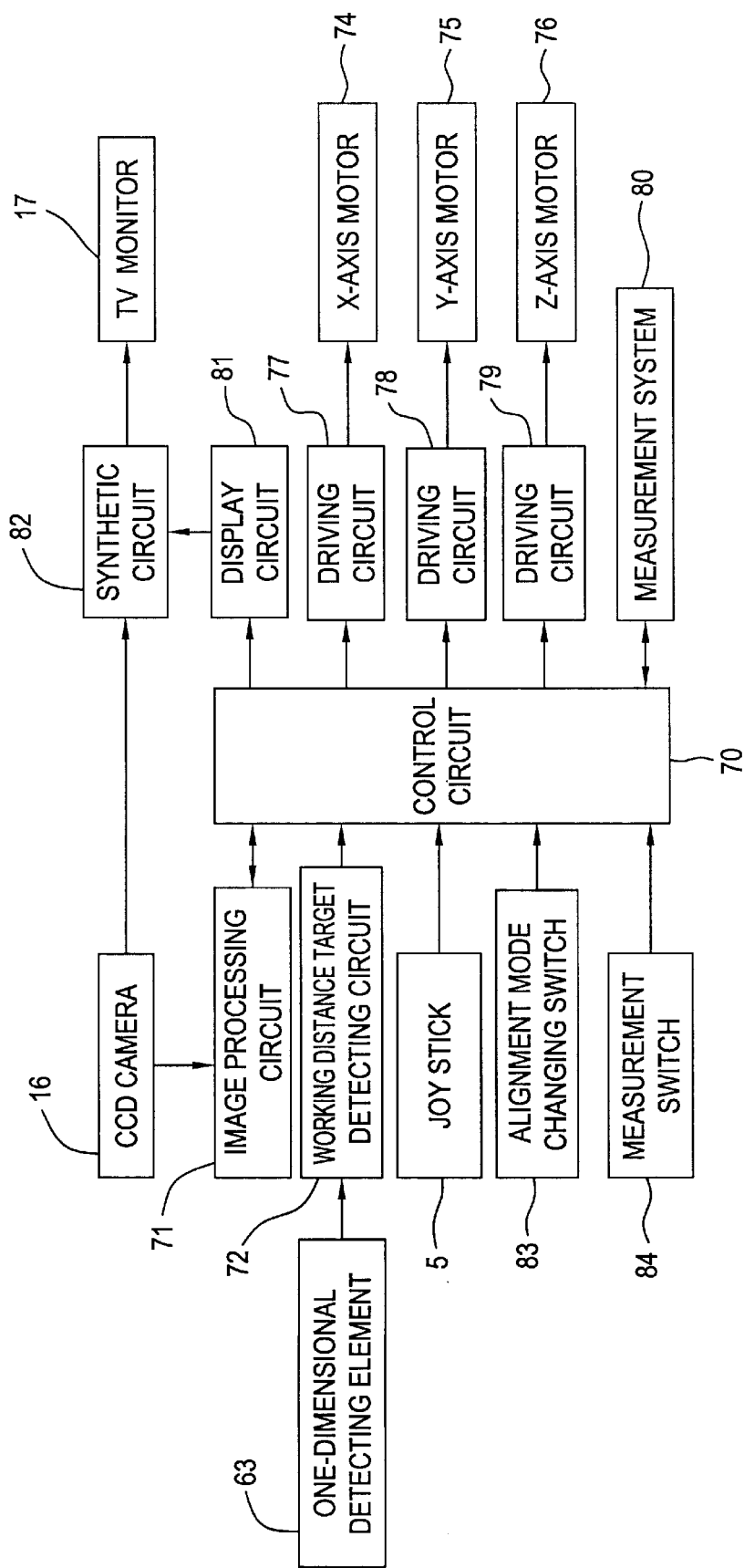
FIG. 3 is a view showing a block diagram for a control system of an important part of a noncontact tonometer of a preferred embodiment.

FIG. 3 is a block diagram for a control system of an important part of the apparatus. 70 is a control circuit, 71 is an image processing circuit, and 72 is a target-distance detecting circuit. 74 to 76 are a X-axis motor, a Y-axis motor and a Z-axis motor, respectively, which make the measurement part 4 drive relative to the body part 3, and 77 to 79 are driving circuits for respective motors, respectively. 80 is a measuring system, 81 is a display circuit which generates character information and figures or the like, and 82 is a synthetic circuit. 83 is an alignment-mode changing switch by which either an auto alignment performed by the apparatus based on the target detection or an operation only by the joystick 5 operated by the examiner is selected. 84 is a measurement switch for use in inputting measurement starting signal.

The image processing circuit 71 gives an image processing to the photographed image transmitted from the CCD camera 16, and inputs the processing result to the control circuit 70. The control circuit 70 obtains the positional information of pupil and targets.

Also, the control circuit 70 obtains the deviation information of forward and backward direction relative to the eye E to be examined based on the signal transmitted from the one-dimensional detecting element 63 through the target-distance detecting circuit 72. The deviation information obtained by the control circuit 70 is sent to the display circuit 81, then the display circuit 81 causes the figure signal of the distance mark and the positional signal on the TV monitor to generate based on the deviation information. The output signal transmitted from the display circuit 81 is synthesized with the screen image signal from the CCD camera 16, then is outputted on the TV monitor 17.

Figure 4:
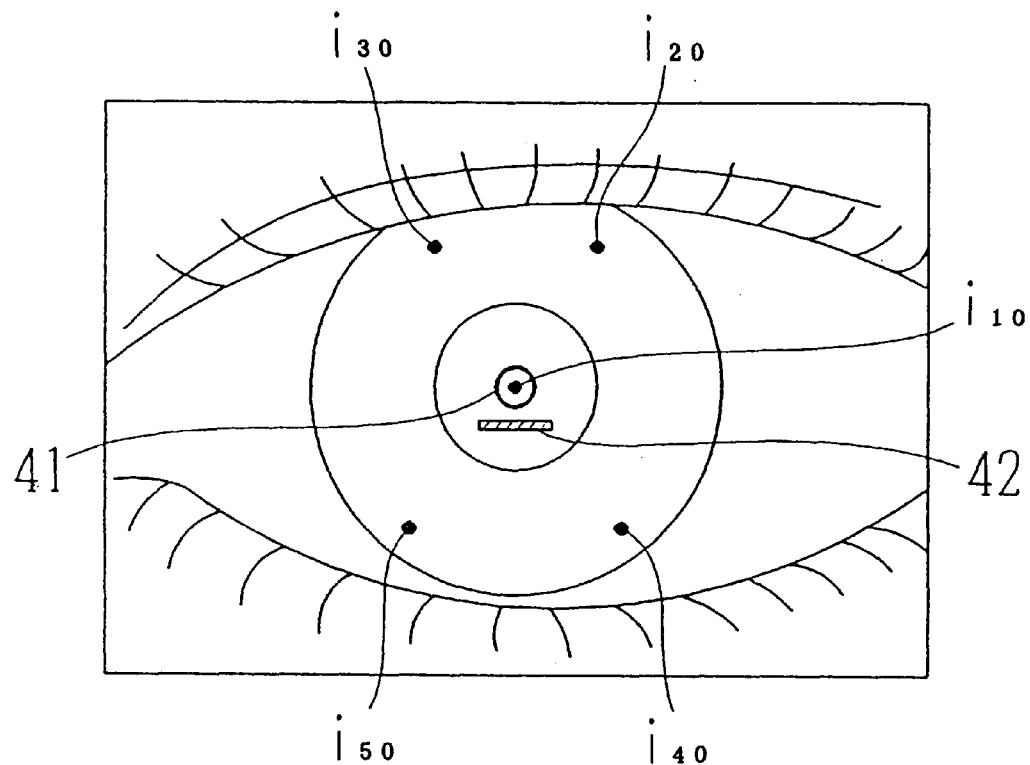
FIG. 4 is a view showing an example of a screen which is displayed at the TV monitor at the time when the eye to be examined is aligned appropriately.

FIG. 4 is a view showing an example of a screen which is displayed at the TV monitor at the time when the XY-direction is aligned appropriate. Under the condition that the XY-direction is aligned appropriate, the four target images $i_{20}$, $i_{30}$, $i_{40}$ and $i_{50}$ which are formed at the periphery of cornea by the second alignment target projecting optical system and the target image $i_{10}$ which is formed close to the cornea center by the first alignment target projecting optical system are displayed. 41 denotes the reticle image. 42 denotes the distance mark which moves vertically on the reticle image 41 corresponding to the distance between the cornea of the eye to be examined and the nozzle part 6, then once the cornea is at the appropriate working distance, the distance mark 42 is superposed on the reticle image 41.

Next, on the basis of the detecting result of the first and second alignment targets, judging method of the alignment condition in order to control the movement of the measurement part 4 in the XY-direction will be described.

Figure 5:
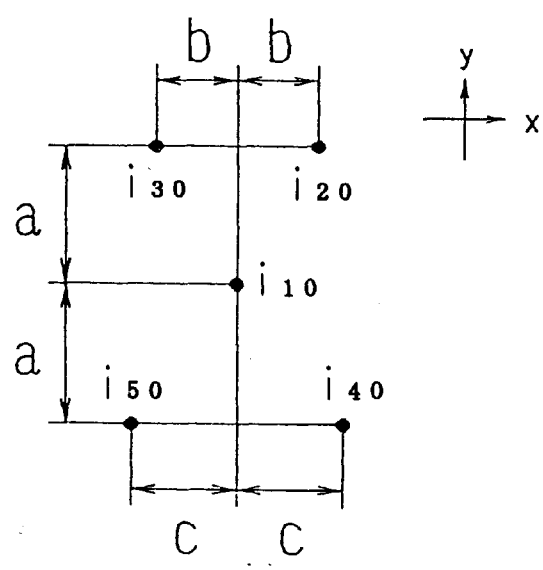
FIG. 5 is a view showing the positional relationships between five target images which are defined as standards in the case of judging the alignment condition.

First of all, the positional relationships between five target images which are defined as standards upon judging the alignment condition will be described referring to FIG. 5. The target images $i_{20}$ and $i_{30}$ are defined as that they are both separated approximately width a to upper direction along the Y-axis direction relative to the target image $i_{10}$ which is aligned to be appropriate condition, and that they are both separated approximately width b to both sides along the X-axis direction relative to the same. The target images $i_{40}$ and $i_{50}$ are defined as that they are both separated approximately width a to lower direction along the Y-axis direction relative to the targets image $i_{10}$ which is aligned to be appropriate condition, and that they are both separated approximately width c to both sides along the X-axis direction relative to the same. These positional relationships and intervals vary to some extent corresponding to the cornea shape and the relative position of the apparatus relative to the eye to be examined, however do not vary in a large scale, therefore these positional relationships and intervals are defined as the judgement standards to specify that which target is detected based on the number and position of the targets. Besides, a, b and c are intervals of the coordinate, which are used for convenience in this description and have no particular sense.

Next, the guidance of the measurement part 4 based on the number and positional relationships of the detected target will be described. Besides, the turn of the target which is used for the description is decided from upper side to lower side of the screen in turn, and concerning the same height, the left one is taken priority.

<In the Case that the Target Image is One from Among Five All>

It cannot be specified that which target causes the target image, therefore the control circuit 70 obtains the XY coordinates of the detected target and makes the measurement part 4 move by driving the X-axis motor 74 and the Y-axis motor 75 so that the target image may move to the standard position (the optical axis of the observation optical system). However, in this case, the purpose is to detect the other target image, therefore once the number of target images which are detected has been increased, the alignment is performed according to the following requirements.

<In the Case that the Target Images are Two from Among Five All>

In the case that the target images are two, it cannot be also specified that which target causes the target images, therefore the control circuit 70 obtains the XY coordinates of the two target images, then controls and makes the measurement part 4 move toward the direction where the other target images can be detected.

<In the Case that the Target Images are Three from Among Five All>

Figure 6:
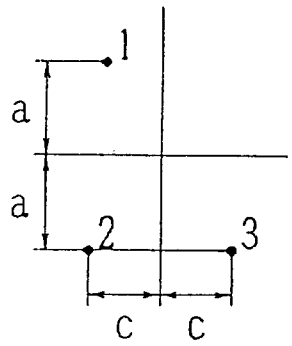
FIGS. 6(a)–6(e) are views showing the positional relationships in the case that three target images are detected.
Figure 6:
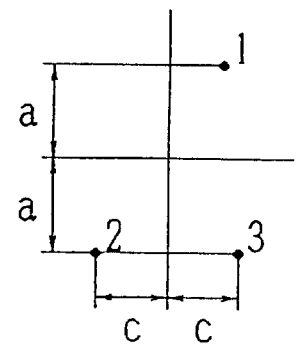
Figure 6:
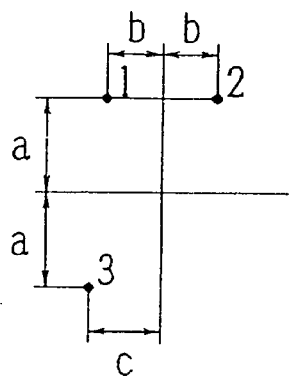
Figure 6:
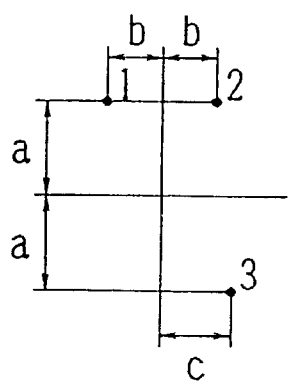
Figure 6:
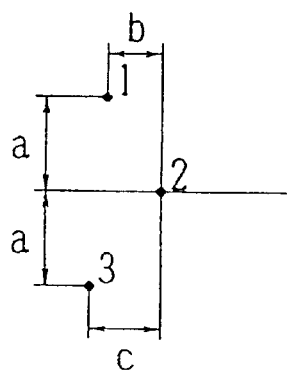

Once the target images are detected not less than three, it comes to be specified that which target among the target images $i_{10}$ to $i_{50}$ causes the target images according to the relationships thereof. The control circuit 70 obtains respectively the XY coordinates (X1, Y1) of the first target image, the XY coordinates (X2, Y2) of the second target image, and the XY coordinates (X3, Y3) of the third target image, thereby the control circuit 70 makes the measurement part 4 move. Besides, the reference numerals shown in FIG. 6, attached to the right-upper position of respective target images in convenience mean the turn of the target images.

[A] In the case that the difference of the Y coordinates between the first target image and the second target image is approximately 2a: There are two cases shown in FIG. 6(a). These cases are under the condition that the target image $i_{10}$ is not detected, however, the control circuit 70 causes the measurement part 4 to move with assuming the cornea center is at the XY coordinates ((X2+X3)/2, (Y1+Y2)/2).

[B] In the case that the difference of the Y coordinates between the first target image and the second target image is approximately a and that the Y coordinates of the second target image and the Y coordinates of the third target image are approximately the same : This is shown in FIG. 6(b). The first one is specified as the target image $i_{10}$, whereby the measurement part 4 is made to move.

[C] In the case that the Y coordinates of the first target image and the Y coordinates of the second target image are approximately the same and that the difference of the Y coordinates between the second target image and the third target image is approximately 2a: There are two cases shown in FIG. 6(c). As the same with FIG. 6(a), the target image $i_{10}$ is not detected, however, the measurement part 4 is made to move with assuming the cornea center is at the XY coordinates ((X1+X2)/2, (Y1+Y3)/2).

[D] In the case that the difference of the Y coordinates between the second target image and the third target image is approximately a and that the Y coordinates of the first target image and the Y coordinates of the second target image are approximately the same: This is shown in FIG. 6(d). The third one is specified as the target image $i_{10}$, whereby the measurement part 4 is controlled and is made to move.

[E] In the case that above requirements are not satisfied: There are four cases shown in FIG. 6(e). In this case, the second one is specified as the target image $i_{10}$, whereby the measurement part 4 is made to move.

<In the Case that the Target Image are Four from Among Five All>

Figure 7:
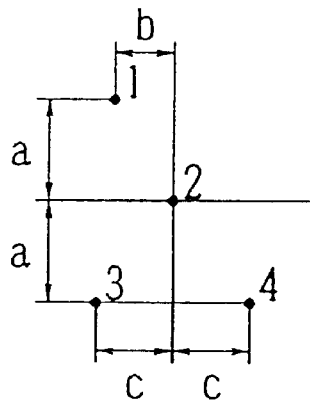
FIGS. 7(a)–7(d) are views showing the positional relationships in the case that four or five target images are detected.
Figure 7:
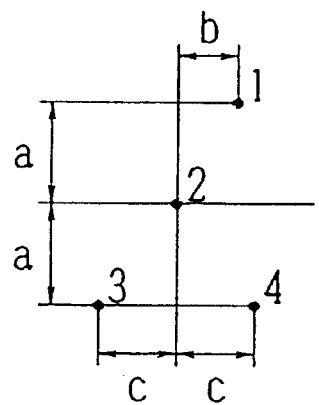
Figure 7:
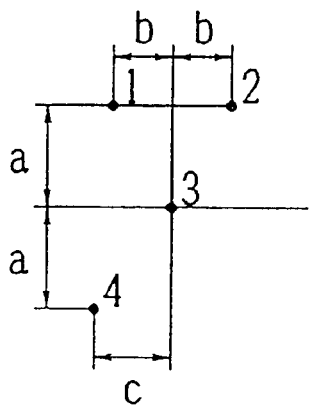
Figure 7:
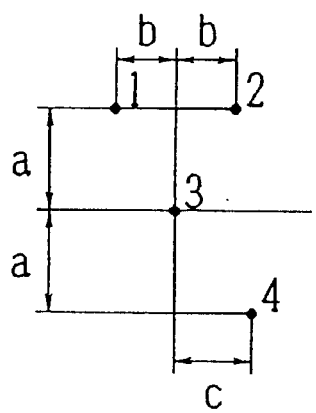
Figure 7:
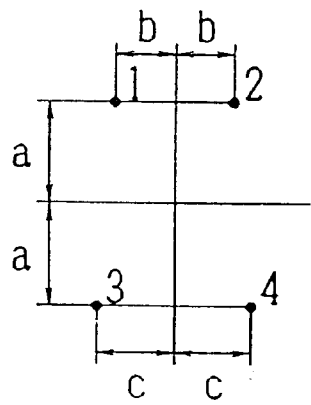
Figure 7:
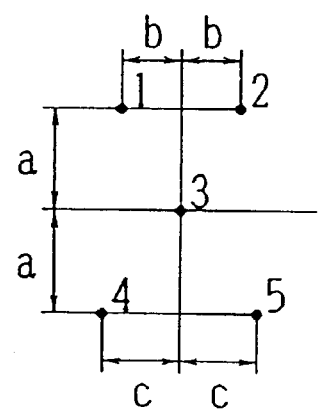

The control circuit 70 obtains the XY coordinates of respective target images, and makes the measurement part 4 move. In the FIG. 7, reference numerals are attached in order to distinguish respective target images.

[A] In the case that the Y coordinates of the first target image and the Y coordinates of second target image are not approximately the same: There are two cases shown in FIG. 7(a). The second one is specified as the target image $i_{10}$, whereby the measurement part 4 is made to move.

[B] In the case that the Y coordinates of the third target image and the Y coordinates of the fourth target image are not approximately the same: There are two cases shown in FIG. 7(b). The third one is specified as the target image $i_{10}$, whereby the measurement part 4 is made to move.

[C] In the case of exclusive above-mentioned A and B: The case is shown in FIG. 7(c). In this case, only target image $i_{10}$ is not detected, therefore the measurement part 4 is made to move with assuming that the cornea vertex is at the midpoint of the four target images, for example, ((X1+X2)/2, (Y1+Y3)/2).

<In the Case that the Target Images are Five from Among Five All>

All target images are detected, therefore the target image $i_{10}$ can be specified, whereby the measurement part 4 is made to move.

Concerning the guidance method of the measurement part 4 based on the number and position of the detected target images, as described above, in the case that the target image $i_{10}$ is detected and specified, it is assumed as a standard in any cases, and in the case that the target image $i_{10}$ is not detected and not specified, the coordinates of other target images are assumed as a standard, whereby the movement is performed. Also, concerning the final judgement of alignment condition of XY-direction, if the target image $i_{10}$ which is detected and specified is within the predetermined permissible limits, it is judged that the alignment has been completed, while all of the five target images are not detected. Besides, the apparatus has the first permissible limits for judging whether the alignment condition of XY-direction has been completed, and the second permissible limits for making the difference to the moving velocity of the measurement part 4 in XY-direction which is set wider than the first permissible limits. The control circuit 70 judges whether the target image $i_{10}$ which is detected or specified is within the second permissible limits or not, in the case out of the limits, the control circuit 70 makes the measurement part 4 move with comparatively high velocity. Thereby the alignment before fine-adjustment can be made quickly.

The operation of the noncontact tonometer having such architecture as described above will be described below. The description is made with making the alignment movement at the time when the auto alignment is selected as the point of the following description.

The examiner fixes the eye to be examined by using the jaw stand 2 and makes the eye to be examined see the fixation target. After the preparation for measurement, the examiner operates the joystick 5 and the like with observing the TV monitor 17, and aligns the measurement part 4 roughly with respect to the eye to be examined. The rough alignment is performed so that at least one target image which is formed by the first and the second alignment target projecting optical system may displayed on the TV monitor 17.

Once the target image is detected, the operation for the joystick 5 is stopped (the message for instructing stop may be displayed, or means for restricting the motion of the joystick 5 may be acted, if necessary).

Figure 8:
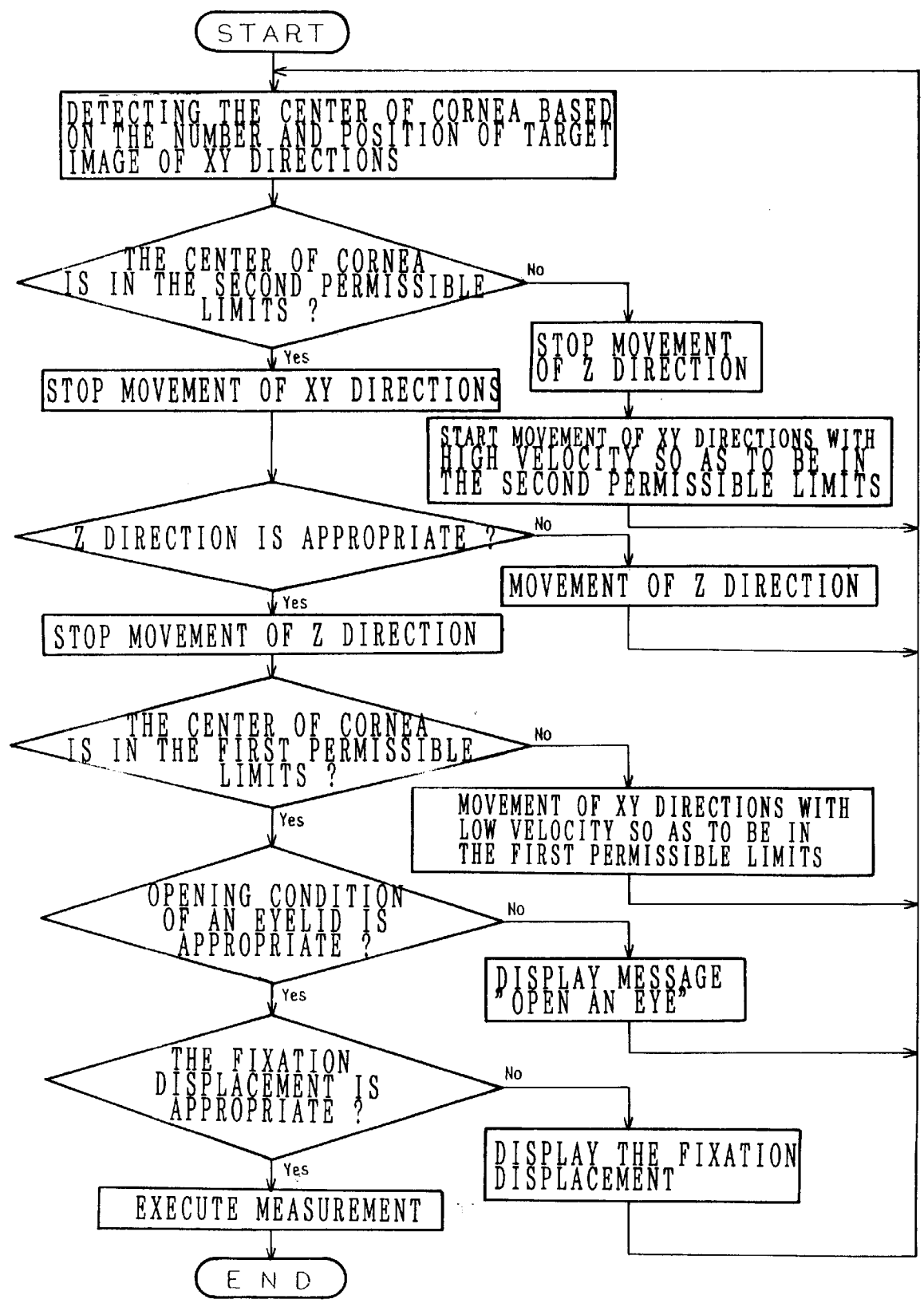
FIG. 8 is a flowchart for describing a routine procedure of an alignment operation after the target images are detected.

The alignment movement after that will be described referring to the flowchart shown in FIG. 8. The control circuit 70 makes the measurement part 4 move by driving the X-axis motor 74 and the Y-axis motor 75 based on the number and positional relationships of above-mentioned target images so that the target image $i_{10}$ may enter the second permissible limits. On the screen of the TV monitor 17, the target image $i_{10}$ comes to enter into the reticle image 41.

Once the target image $i_{10}$ enters into the second permissible limits, the control circuit 70 stops driving in XY-direction and judges the suitability of the working distance. The light bundle of the target $i_6$ by the distance target projecting optical system comes to transmit into the one-dimensional detecting element 63, and then the control circuit 70 obtains the deviation information of Z-direction based on the signals transmitted from the one-dimensional detecting element 63 and makes the measurement part 4 move backward and forward direction based on the deviation information by driving the Z-axis motor 76. Also, a distance mark 42 is displayed on the TV monitor 17 which moves simultaneously up and down over the reticle image 41 as the measurement part 4 moves forward and backward direction (in the case that the distance mark 42 is not displayed, the joystick 5 comes to be able to use, then the examiner performs the forward and backward adjustment so as to be in the direction where the target image $i_{10}$ is brought into focus).

Once the Z-direction comes to be appropriate condition, the control circuit 70 stops the movement of the measurement part 4 in forward and backward direction, and judges whether the target image $i_{10}$ is within the first permissible limits or not. In the case out of the limits, the measurement part 4 is made to move during the predetermined time to perform fine-adjustment so that the target image $i_{10}$ may enter into the first permissible limits. The movement velocity is slower than above-mentioned movement of XY-direction (in the case of bringing into the second permissible limits). Thereby the fine-alignment of XY-direction can be performed easily with keeping the condition that the target image $i_{10}$ does not pass through the first permissible limits.

Once the target image $i_{10}$ enters into the first permissible limits whereby the alignment condition of XY-direction comes to be appropriate, the suitability judgement for condition of eyelid-opening is performed. This judgement is performed under the condition that at least the target image $i_{20}$ or $i_{30}$ is detected within the predetermined area, then is performed by judging whether the light volume output level thereof is not less than the predetermined value or not. Unless the condition of eyelid-opening is not sufficient, light bundles emitted from the light sources 7a and 7b form no images, and are reflected and diffused, therefore the light bundle of target $i_2$ or $i_3$ enters with spreading on the photographing element of the CCD camera 16. Therefore the condition of eyelid-opening can be detected based on whether the light volume output within the predetermined area is not less than the predetermined level or not. The detection of the condition of eyelid-opening is the same basically as the Japanese Patent Application No.HEI7-337909 corresponding to U.S. patent application Ser. No.08/755,646 by the applicant of the present invention, so see this reference.

Figure 9:
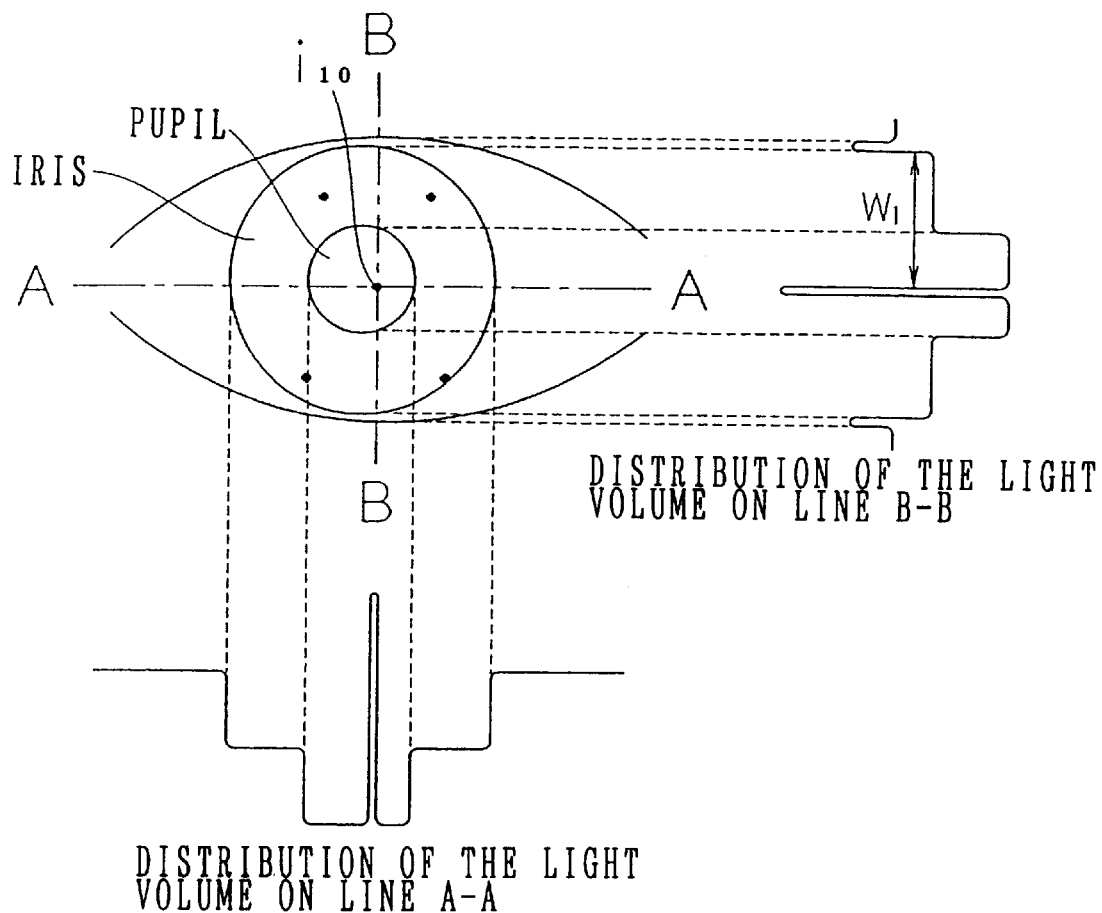
FIGS. 9(a) and 9(b) are views showing a level of reflecting light volume in XY-axis directions of the eye to be examined.
Figure 9:
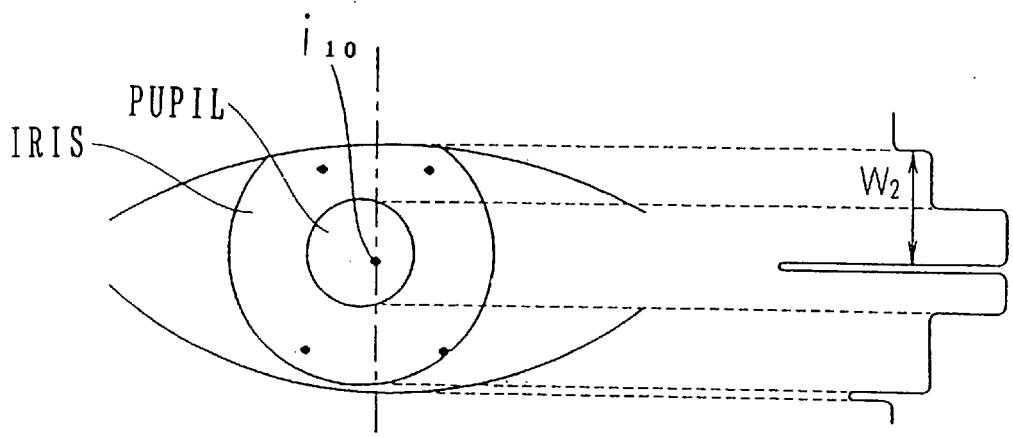

If no problems are found in the condition of the eyelid-opening, the suitability judgement for eye-fixation deviation is performed as following. The control circuit 70 fetches the signal on the line A—A of X-axis direction and the line B—B of Y-axis direction passing the target $i_{10}$ from the photographing signals transmitted from the CCD camera 16 as shown in FIG. 9(a). Since the respective reflective light volume levels of target image $i_{10}$, the pupil, the iris, and the sclera are different, the boundary edge of the pupil (or the iris) is detected by the image processing. The control circuit 70 compares the distances up to the detected boundary edges on the line A—A and the line B—B from the target image $i_{10}$ whereby it is judged whether the differences of both of the distance are within permissible limits or not, and is judged whether the target $i_{10}$ is at approximately center of both boundaries of the pupil or not. Once it is confirmed that the target $i_{10}$ is at approximately center of both boundaries of the pupil concerning both the line A—A and the line B—B, it is judged that no eye-fixation deviation is found. If a deviation is found at least in either case, it is judged that the eye-fixation is deviated, then the matter is displayed on the TV monitor. Besides, whether the eye-fixation is deviated or not may be also judged based on the degree of deviation between the target image $i_{10}$ and the center of pupil by obtaining the coordinates of the center of pupil based on the boundary edge of pupil.

Also, the suitability judgement for condition of the eyelid-opening may be performed by fetching the signal on line B—B in Y-axis direction in the same way as the suitability judgement for eye-fixation deviation and then using the difference between the light volume levels, without using the detected condition of the target image. That is, as shown in FIG. 9(b), in the case that the width of the iris does not secured more than the necessary area of measurement, it is judged that the condition of eyelid-opening is insufficient based on the light volume signal of Y-axis direction.

If no problems are found concerning the condition of eyelid-opening and the eye-fixation deviation, and at the same time, the target image $i_{10}$ is within the first permissible limits, the control circuit 70 sends the measurement starting signal automatically with defining that the measurement starting requirements are satisfied, thereby the measurement caused by the measurement system 80 is executed (it is also allowed that the completion of alignment may be displayed on the TV monitor, or sounds may inform the matter of the examiner, thereby the examiner presses the measurement starting switch 84, then the measurement is executed).

In above-mentioned preferred embodiment, the movement of the measurement part 4 is controlled from three directions of XYZ, it may be controlled from only XY directions, or in the case that it is controlled by the manual operation using the joystick 5 of the examiner, guidance may be performed by displaying an allow post or the indicating marks decided in advance or the like which are used for informing the movement direction of the examiner on the TV monitor. Also, it may be allowed that the examiner select the alignment control for the apparatus.

Still, in above-mentioned preferred embodiment, the target images which are projected onto the periphery of cornea of the eye to be examined is decided four, however, if at least two target images are projected, the alignment condition can be judged. The target images which are projected may be allowed more than four.

Besides, in above-mentioned guidance method for the measurement part 4, the target image $i_{10}$, is specified based on the positional relationships of the target images, therefore there is some possibility of specifying the other target image or disturbance light as the target image $i_{10}$ due to the disturbance light. In this case, since guidance of the measurement part 4 comes to be unstable, even if it is specified as the target image $i_{10}$, unless the target image does not exist within the predetermined range with the center at the standard position on the CCD camera 16 (within the range corresponding to the diameter of the nozzle 9), it is made so as not to move. Thereby the incorrect action of the automatic alignment is prevented.

[The Second Preferred Embodiment]

Referring to the first preferred embodiment, in the case that the target image is one from among five all and in the case that the target images are two from among five all, unless the target image cannot be specified, the measurement part 4 is guided to the direction where other target images can be detected, however, referring to this way, the measurement part 4 does not move so that the center axis of the measurement part 4 can coincide with the cornea center, therefore the measurement part 4 does not necessarily move to the direction where the target image $i_{10}$ corresponding to the center position of the cornea can be detected. Therefore, in the case that the fluctuations in number of the target detection due to the condition of the eyelid-opening and a blink of the eye to be examined, or in the case that light bundle of the target $i_1$ is interrupted by the nozzle 9, the guidance of the measurement part 4 comes to be unstable, therefore in some cases, it takes much time for alignment. In this case, if the guidance method as following is adopted, the incorrect action of alignment can be deteriorated.

<In the Case that the Target Image is One from Among Five All>

Only in the case that the detected target image is specified as the target image $i_{10}$, the measurement part 4 is made to move, in the case that it is not specified as the target image $i_{10}$, the measurement part 4 is made not to move. When the detected target image satisfies the next requirements, the target image is specified as the target image $i_{10}$.

① The detected target image exists within the predetermined range (for example, within a size corresponding to the diameter of the nozzle 9) with the center at the standard position. ② Further, the deviation of Z direction is within the predetermined range relative to the appropriate working distance (the image of the target $i_6$ due to the distance target projecting optical system 50 can be detected by the one-dimensional detecting element 63 and the deviation thereof is within the predetermined range).

<In the Case that the Target Images are Two from Among Five All>

Even if the target images are two, it comes to be specified that which target among the target images causes the target images according to relationships thereof by modifying the optical system which forms the target image. For example, the arrangement for the second alignment target projecting optical system 7 is desired as following, that is, in FIG. 5, the width b of the target images $i_{20}$ and $i_{30}$ is desired so as to be smaller than the width c of target images $i_{40}$ and $i_{50}$ (but so as not to be a half of the width c). Thereby it is specified that which targets causes the target images by observing the coordinates position of the two target images which can be detected, as following.

Figure 10A:
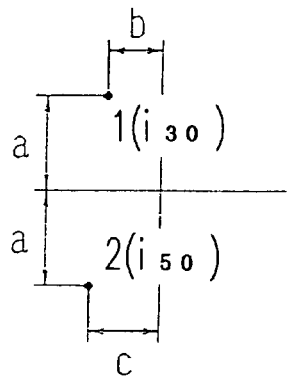
FIGS. 10A(a) and 10A(b) are views showing the first combination to specify one target image in the case that two target images are detected.
Figure 10A:
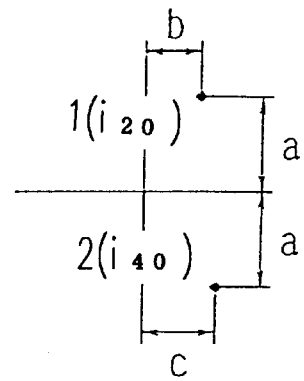

[A] In the case that the difference of the X coordinates between the first target image and the second target image is small (not more than the width b) and that the difference of the Y coordinates between the first target image and the second target image is large (approximately width 2*a*): As shown in FIG. 10A(*a*) and (b), there are two cases, the one is the combination of the target images $i_{20}$ and $i_{40}$ and the other is the combination of the target images $i_{30}$ and $i_{50}$. Further, these two cases are distinguished as following.

① In the case of the X coordinates of the first one>the X coordinates of the second one: It can be judged as $i_{30}$ and $i_{50}$.

② In the case of the X coordinates of the first one<the X coordinates of the second one: It can be judged as $i_{20}$ and $i_{40}$.

Figure 10B:
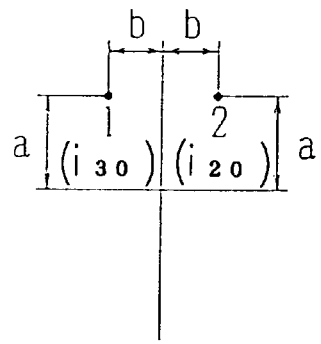
FIGS. 10B(a) and 10B(b) are views showing the second combination to specify one target image in the case that two target images are detected.
Figure 10B:
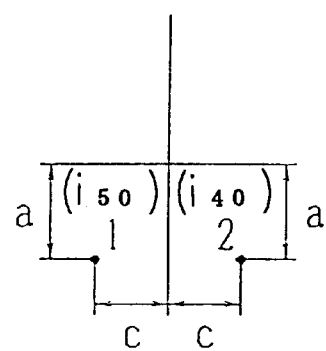

[B] In the case that the difference of Y coordinates between the first target image and the second target image is approximately the same: As shown in FIG. 10B(a) and (b), there are two cases, the one is the combination of the target images $i_{20}$ and $i_{30}$ and the other is the combination of the target images $i_{40}$ and $i_{50}$. Further, these two cases are distinguished as following.

① In the case of the difference of X coordinates between the first one and the second one≦the width 2*b*: It can be judged as $i_{20}$ and $i_{30}$.

Figure 10C:
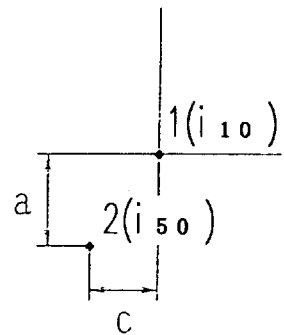
FIGS. 10C(a) and 10C(b) are views showing the third combination to specify one target image in the case that two target images are detected.
Figure 10C:
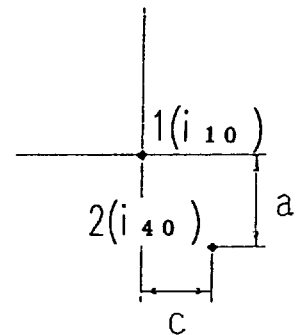

② In the case of the difference of X coordinates between the first one and the second one>the width 2*b*: It can be judged as $i_{40}$ and $i_{50}$. [C] In the case that the difference of Y coordinates of the first target image and the second target image is approximately a and that only the first target image is within the predetermined range relative to the standard position (center optical axis) as the center: As shown in FIG. 10C(a) and (b), there are two cases, the one is the combination of the target images $i_{10}$ and $i_{40}$ and the other is the combination of the target images $i_{10}$ and $i_{50}$, in either case, the first one is specified as the target image $i_{10}$.

Figure 10D:
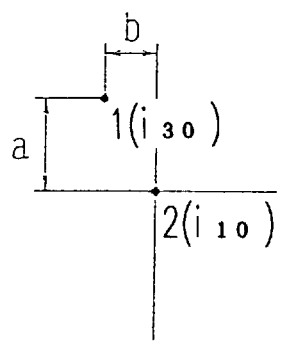
FIGS. 10D(a) and 10D(b) are views showing the fourth combination to specify one target image in the case that two target images are detected.
Figure 10D:
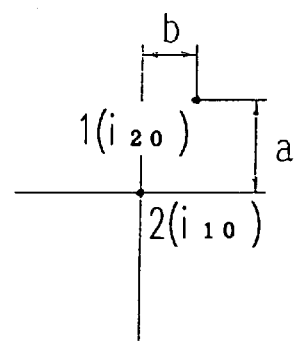

[D] In the case that the difference of the Y coordinates between the first target image and the second target image is approximately a and that only the second target image is within the predetermined range relative to the standard position (center optical axis) as the center: As shown in FIG. 10D(a) and (b), there are two cases, the one is the combination of the target images $i_{10}$ and $i_{20}$ and the other is the combination of the target images $i_{10}$ and $i_{30}$, in either case, the second one is specified as the target image $i_{10}$.

Figure 10E:
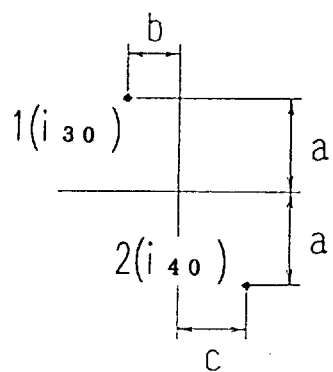
FIGS. 10E(a) and 10E(b) are views showing the fifth combination to specify one target image in the case that two target images are detected.
Figure 10E:
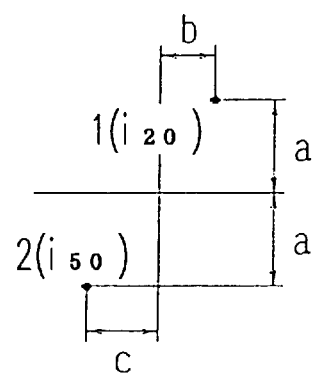

[E] In the case that the difference of the X coordinates between the first target image and the second target image is not approximately the same, and that the difference of the Y coordinates between the first target image and the second target image is large (approximately 2a) As shown in FIG. 10E(a) and (b), there are two cases, the one is the combination of the target images $i_{20}$ and $i_{50}$, and the other is the combination of the target images $i_{30}$ and $i_{40}$.

Next, the guidance method based on the pattern of the target image specified as described above and the positional relationships thereof for the measurement part 4 will be described.

Firstly, in the case of the pattern by which the target image $i_{10}$ is specified as described above-mentioned [C] and [D], the measurement part 4 is guided based on this matter.

In the case of the pattern by which the target image $i_{10}$ cannot be specified, the XY coordinates of the cornea center is inferred from the two target images, then the measurement part 4 is guided based on the position of the coordinates. For example, the Y coordinates of the cornea center at the time when the target images $i_{30}$ and $i_{50}$ are specified as described above-mentioned [A] ① is found as [(Y1+Y2)/2]. While, if the target image $i_{30}$ is considered as a standard, the X coordinates is found as [X1+b] by adding the width b to X1 of the X coordinates thereof briefly. However, the value tends to be incorrect due to the individual-difference of the cornea size. The position of coordinates of respective target images varies in proportion to the size variation of cornea curvature generally. This relationships is utilized for finding the X coordinates, therefore in stead of width b, the value found by multiplying the Y-coordinates interval between the target images $i_{30}$ and $i_{50}$ by a constant $\alpha$ is added to the X1 which is the X coordinates of the target image $i_{30}$ (or is added to the X2 which is the X coordinates of the target image $i_{50}$). That is, the X coordinates in this case can be defined as [X1+(Y2−Y1)×$\alpha$]. In this way, the coordinates of center position of cornea with higher accuracy can be inferred compared with the case of just adding a constant. Besides, a constant $\alpha$ is desired in advance according to the arrangement relationships between the target projecting system and the detecting system.

As the same way, the XY coordinates of center position of cornea at the time when the target images $i_{20}$ and $i_{40}$ are specified are (X1−(Y2−Y1)×$\alpha$, (Y1+Y2)/2).

Also, based on the same idea, the XY coordinates of the cornea center at the time when they are specified as the target images $i_{20}$ and $i_{30}$ of [B] ① are ((X1+X2)/2, Y1+(|X1−X2|)×$\beta$). The XY coordinates of the cornea center at the time when they are specified as the target images $i_{40}$ and $i_{50}$ of [B] ② are ((X1+X2)/2, Y1−(|X1−X2|)×$\gamma$). Where the constants $\beta$ and $\gamma$ are also desired in advance.

As above-mentioned [E], the XY coordinates of the cornea center at the time when the combination of target images $i_{20}$ and $i_{50}$ and the combination of target images $i_{30}$ and $i_{40}$ are specified as ((X1+X2)/2, (Y1+Y2)/2).

As described above, under the condition that the target images which can be detected are only two, in the case that it is judged as the target image $i_{10}$, it is used as standard, or in the case that the target image $i_{10}$ cannot be specified, if the measurement part 4 is guided based on the center position of cornea found by using the two target images, the measurement part 4 always comes to move so as to cause the center axis of the measurement part 4 to coincide with the cornea center. Thereby the guidance of the measurement part 4 is made to be stable.

[The Third Preferred Embodiment]

Referring to the first preferred embodiment (including the second preferred embodiment), the suitability of the alignment in XY direction is judged by detecting the target image $i_{10}$ finally. If the condition of the cornea surface is fine, the reflecting light of the alignment target from the cornea center has sufficient brightness and size, therefore the detection of the target image $i_{10}$ is relatively easy. However, in the case that the cornea surface is deformed for some reason or other such as an eye disease patient caught by a laceration of the cornea surface, a dry eye, IOL inserted-eye, and a postoperative glaucoma, even if the alignment has been completed originally, the reflecting light (the target image $i_{10}$) of the alignment target from the cornea center is not often obtained with sufficient brightness and size. In this case, referring to the detection method by the first and second preferred embodiments, sometimes the judgement of alignment in XY direction cannot be performed. Particularly, referring to such establishment that the measurement is started automatically based on the detection of the completed condition of alignment, it is far from easy to start measurement.

Figure 11:
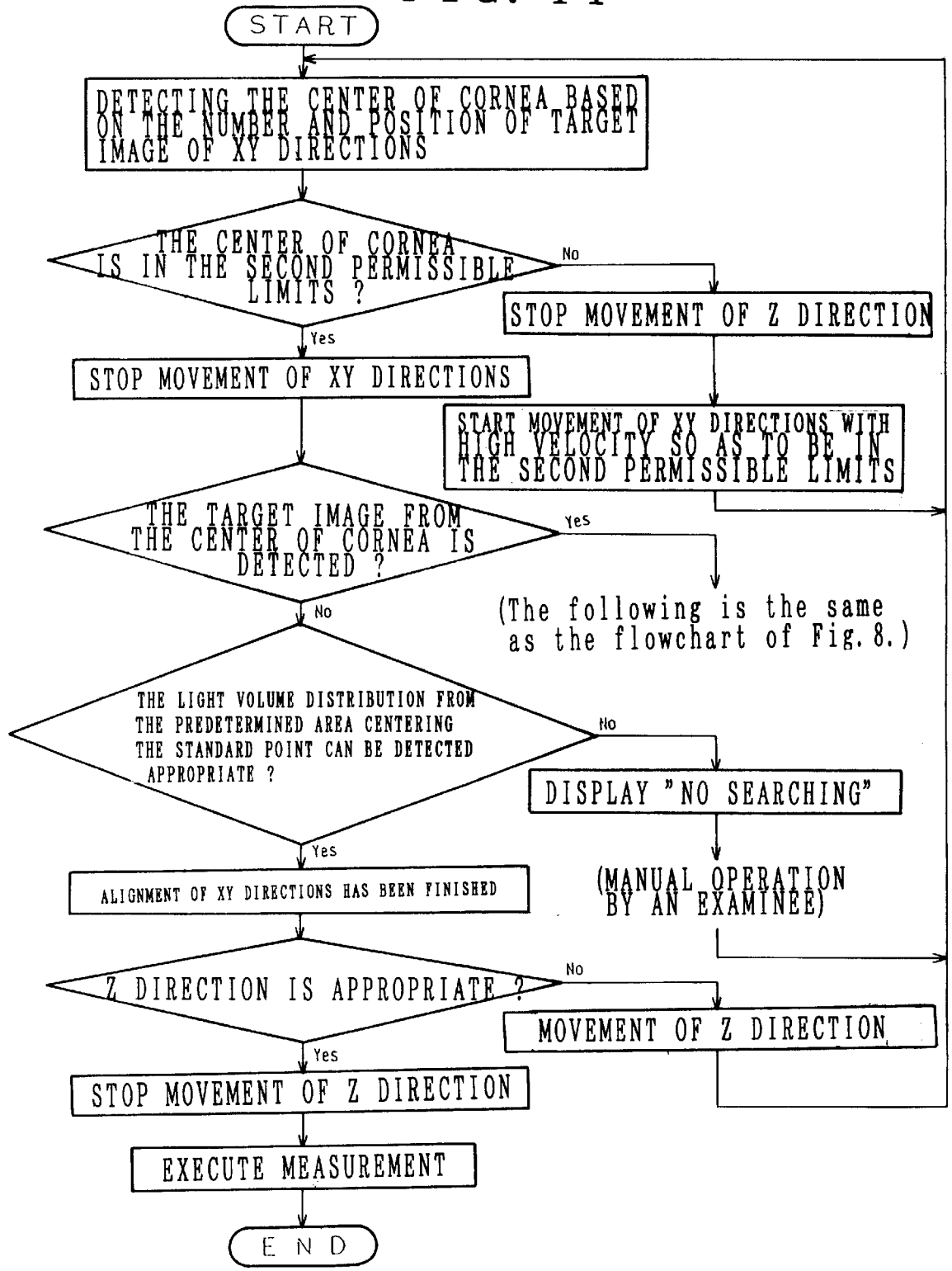
FIG. 11 is a flowchart for describing a routine procedure of alignment operation of the third preferred embodiment.
Figure 12:
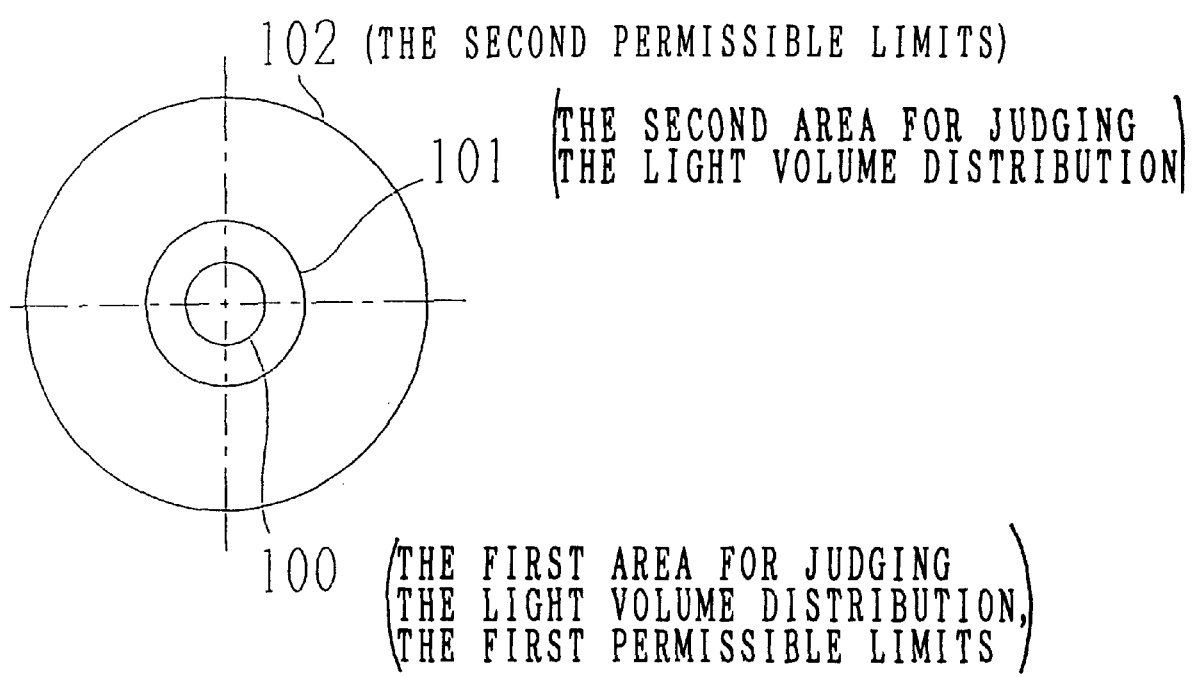
FIG. 12 is a view showing an example of the judging area to judge the alignment of XY directions based on the distribution of light volume.

The alignment operation in such case will be described based on the flowchart shown in FIG. 11. The apparatus detects the center position of cornea based on the number and position of the target image, then makes the measurement part 4 based on the position move so that the cornea center enters the second permissible limits (same as the first preferred embodiment). If the reflecting light of the target from the cornea center is not less than a standard light volume level, it is detected as the target image $i_{10}$, however, if it is below a standard light volume level, the alignment of the XY direction is judged based on whether the distribution of light volume in the predetermined area with the center at the standard position on the CCD camera 16 is under the expected condition or not. This judgement is performed in a manner that, for example, as shown in FIG. 12, firstly, the first area 100 for judging the light volume distribution (same area as the first alignment permissible limits as above-mentioned) and the second area 101 for judging the light volume distribution which is wider than the first area 100 (smaller area than above-mentioned second permissible limits) are desired, then the light volume distribution of the first area 100 and that of the second area 101 are observed. Once the light volume which satisfies the degree enough to judge that it is the reflecting light of alignment target is obtained in the second area 101, at the same time, once the light volume not less than the predetermined level is obtained in the first area 100, it can be judged that the reflecting image of the alignment target exists with the center at the standard position on the CCD camera 16. That is, it is judged whether the condition of the alignment in the XY direction has been completed or not. In the case that the alignment has not been completed, the matter that auto alignment is not performed is informed of the examiner by displaying "NO SEARCHING" on the TV monitor 17. The examiner makes the measurement part 4 move by operating the joystick 5 with observing the reflecting image of the alignment target which is displayed on the TV monitor 17.

Once it is judged that the alignment of XY directions has been completed based on the light volume distribution from the predetermined area with the center at the standard point, the apparatus judges the suitability of the Z direction, as a result, if there is deviation, the measurement part 4 is made to move to the Z direction whereby the measurement is performed automatically by causing the alignment of the Z direction to be completed. The detection of the Z direction, even if the part around the cornea center is deformed, the detection can be performed easily by projecting the target light bundle onto the whole of the cornea and then by detecting the reflecting light bundle thereof without being affected by the change of the cornea surface condition.

Further, in the case that the apparatus cannot judge the alignment completion of the XY directions, the measurement is executed by pressing the measurement switch 84 based on the examiner's judgement.

Besides, in the case that the reflecting light of the alignment target from the cornea center is weak, the detecting condition such that the standard light volume levels which is just used for judging the target image is made to be lowered, or the like may be changed.

The present invention may be embodied in other specific forms without departing from the spirit or essential characteristics thereof.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. An ophthalmic apparatus having measurement means for inspection or measurement, that brings said measurement means into a predetermined positional relationship relative to an eye to be examined, comprising:

moving means that moves said measurement means relatively to the eye in vertical and lateral directions;

alignment target projecting optical system that projects plural alignment targets onto the periphery of a cornea of the eye under the condition where a measurement axis of said measurement means approximately coincides with a visual axis of the eye;

alignment target detecting optical system that detects target images formed by said alignment target projecting optical system;

memory in which positional relationships of the detected target images are stored;

judging means having a program that can judge a direction to move by comparison of the stored positional relationships with number and positional relationships of the detected target images when a number of the detected target images is smaller than a number of the projected alignment targets; and a control unit that gives a driving signal to said moving means based on a result judged by said judging means.

2. An ophthalmic apparatus according to claim 1, wherein said judging means includes calculating means that obtains a position at which the measurement axis of said measurement means should be positioned relative to the eye based on the number and the positional relationships of the detected target images and the stored positional relationships, and alignment permissible limits desiring means that sets first alignment permissible limits and second alignment permissible limits, which are set wider than said first alignment permissible limits relative to said measurement axis; and wherein said control unit controls said moving means so that moving velocity entering into said second alignment permissible limits is faster than moving velocity entering into said first alignment permissible limits.

3. An ophthalmic apparatus according to claim 1, further comprising:

central alignment target projecting optical system that projects a central alignment target from a direction of said measurement axis to a corneal center of the eye under the condition where said measurement axis approximately coincides with said visual axis; and central alignment target detecting optical system that detects a target image of said central alignment target, wherein said memory stores positional relationships of the target images detected by said alignment target detecting optical system and said central alignment target detecting optical system.

4. An ophthalmic apparatus according to claim 4, wherein said center alignment target detecting optical system is shared with said alignment target detecting optical system.

5. An ophthalmic apparatus according to claim 1, wherein said target projecting optical system projects four alignment targets to different parts of the periphery of the eye.

6. An ophthalmic apparatus according to claim 1, further comprising:

photographing means that photographs an image for observing an anterior part of the eye; and display means that displays the image photographed by said photographing means.

7. An ophthalmic apparatus according to claim 1, wherein said moving means includes manual moving means for moving said measurement means by manual operation by an examiner, and said apparatus further comprising:

moving direction displaying means for displaying the moving direction of said moving means.

8. An ophthalmic apparatus according to claim 1, further comprising:

working distance target projecting optical system that projects a target for detecting a working distance onto the eye;

working distance target detecting optical system that detects a target image of said working distance target;

working distance judging means that judges suitability of alignment condition of the working distance based on a result detected by said working distance target detecting optical system;

eyelid-opening sensing means for sensing whether an eyelid exist within predetermined limits at the time when the alignment has been completed; and measurement starting-signal generating means for generating a measurement starting-signal for making said measurement means go into run at the time when condition of eyelid-opening is judged sufficient by said eyelid-opening sensing means.

9. An ophthalmic apparatus according to claim 8, wherein said eyelid-opening sensing means includes an eyelid-opening target projecting optical system that projects a target for detecting the eyelid-opening onto the periphery of the cornea of the eye, and eyelid-opening target detecting optical system that detects a target image formed by projecting said eyelid-opening target.

10. An ophthalmic apparatus according to claim 9, wherein said eyelid-opening target projecting optical system is shared with said alignment target projecting optical system and/or said eyelid-opening target detecting optical system is shared with said alignment target detecting optical system.

11. An ophthalmic apparatus according to claim 1, wherein said alignment target detecting optical system includes photographing means which photographs an anterior part of the eye, and the apparatus further comprising:

pupil sensing means that detects a boundary of a pupil of the eye by processing a signal transmitted from said photographing means; and eye-fixation judging means that judges suitability of condition of eye-fixation of the eye based on results detected by said pupil sensing means and said alignment target detecting optical system.

12. An ophthalmic apparatus according to claim 1, further comprising:

calculating means that corrects difference of a cornea curvature based on intervals of the target images detected by said alignment target detecting optical system.

13. An ophthalmic apparatus according to claim 1, further comprising:

central alignment target projecting optical system that projects a central alignment target from a direction of said measurement axis to a corneal center of the eye under the condition where said measurement axis approximately coincides with said visual axis, wherein said alignment target detecting optical system detects a target image of the central alignment target formed by said central alignment target projecting optical system, and said judging means judges suitability of alignment condition in vertical and lateral directions based on distribution condition of light volume of the target image of the central alignment target detected by said alignment target detecting optical system.

14. An ophthalmic apparatus according to claim 13, wherein said judging means judges whether the target image of said central alignment target is detected within a level of a predetermined standard light volume in a predetermined area by said alignment target detecting optical system, then in the case that the target image of said central alignment target is not detected within the level of the predetermined standard light volume in the predetermined area, said judging means judges the suitability of the alignment condition based on said distribution condition of light volume.

15. An ophthalmic apparatus according to claim 1, further comprising:

second moving means that moves said measurement means relatively to the eye in backward and forward directions;

a working distance target projecting optical system that projects a target for detecting a working distance onto the eye;

a working distance target detecting optical system that detects a target image of said working distance target; and working distance judging means that judges suitability of alignment condition of the working distance based on a result detected by said working distance target detecting optical system, wherein said control unit gives a driving signal to said second moving means based on a result judged by said working distance judging means.

16. An ophthalmic apparatus having a measurement unit, which inspects or measures an eye to be examined, and that brings said measurement unit into a predetermined positional relationship relative to the eye, comprising:

a moving mechanism having a motor and a driver that move said measurement unit relatively to the eye in vertical and lateral directions;

an alignment target projecting optical system having plural light sources that project plural alignment targets onto the periphery of a cornea of the eye under the condition where a measurement axis of said measurement unit approximately coincides with a visual axis of the eye;

an alignment target detecting optical system having a photo-detector that detects target images formed by said alignment target projecting optical system;

a memory in which positional relationships of the detected target images is stored; and a control unit having a program that can determine a direction to move by comparison of the stored positional relationships with number and positional relationships of the detected target images when the detected target images is smaller than the projected alignment targets in number, and that gives a driving signal to said driver based on the determined result.

* * * * *